United States Patent [19]
Dahle

[11] Patent Number: 5,230,170
[45] Date of Patent: Jul. 27, 1993

[54] ROOT WARMER INSOLE AND METHOD

[76] Inventor: Robert S. Dahle, 848 Amigos, Apt. H, Newport Beach, Calif. 92660

[21] Appl. No.: 892,614

[22] Filed: May 29, 1992

Related U.S. Application Data

[63] Continuation of Ser. No. 615,990, Nov. 20, 1990, abandoned, which is a continuation-in-part of Ser. No. 506,623, Apr. 6, 1990, abandoned.

[51] Int. Cl.$^5$ ................................................ A43B 7/04
[52] U.S. Cl. ............................................. 36/26; 36/43
[58] Field of Search ........................... 36/2.6, 44, 43

[56] References Cited

U.S. PATENT DOCUMENTS

| | | | |
|---|---|---|---|
| 2,675,630 | 4/1954 | Youmans | 36/2.6 |
| 2,680,918 | 6/1954 | Behner | 36/2.6 |
| 3,493,986 | 2/1970 | Erwin | 12/142 |
| 3,585,736 | 6/1971 | Polichena | 36/2.6 |
| 4,023,282 | 5/1977 | Ziegelheafer | 36/2.6 |
| 4,249,319 | 2/1981 | Yoshida | 36/2.6 |
| 4,331,731 | 5/1982 | Seike et al. | 36/2.6 |
| 4,658,515 | 4/1987 | Oatman | 36/44 |
| 4,686,993 | 8/1987 | Grumbine | 36/43 |

FOREIGN PATENT DOCUMENTS

| | | | |
|---|---|---|---|
| 316531 | 5/1918 | Fed. Rep. of Germany | 36/2.6 |
| 3342276 | 11/1985 | Fed. Rep. of Germany | 36/2.6 |
| 3544856 | 12/1985 | Fed. Rep. of Germany | 36/2.6 |
| 971950 | 1/1951 | France | 36/2.6 |
| 122981 | 10/1927 | Switzerland | 36/2.6 |

OTHER PUBLICATIONS

WO 8706803, Nov. 1987, PCT, Ledjeff, 36/2.6.

*Primary Examiner*—Steven N. Meyers
*Attorney, Agent, or Firm*—Sherman & Sherman

[57] ABSTRACT

An insole for a boot or the like has a cavity in the padding layer for holding a heat source that produces heat from an exothermic chemical reaction. The cavity is preferably located in the toe portion of the padding layer. The upper layer of the insole preferably has a plurality of holes therein for facilitating heat transfer from the heat source to the foot of a person using the insole. A pull cord may be connected to the stabilizer layer for facilitating removal of the insole from a boot or the like.

9 Claims, 2 Drawing Sheets

ROOT WARMER INSOLE AND METHOD

This is a continuation of application Ser. No. 615,990, filed on Nov. 20, 1990, for a FOOT WARMER INSOLE AND METHOD now abandoned. Which is a continuation-in-part of applicant's copending application Ser. No. 506,623, filed Apr. 6, 1990, abandoned.

BACKGROUND OF THE INVENTION

This invention relates generally to footwear and particularly to apparatus and methods for keeping a person's feet warm when the ambient temperature is considerably less than normal human body temperature. Still more particularly, this invention relates to an insole for use inside boots, shoes or the like for holding a heat source to provide warmth to the wearer's feet.

Various attempts have been made to keep a person's feet warm in cold environments. Improved insulation and waterproof footwear are helpful in preventing cold feet. However, many individuals still experience discomfort and risk of injury from cold feet in outdoor activities during cold weather because insulation only retains body heat without providing any source of heat.

One attempt to provide a heat source in a boot or the like involves placing an electric heating element in the boot liner and using a battery to supply energy to the heating element. Another attempt to solve the problem of cold feet has involved the use of electrical heating elements in socks. Foot warming devices that use electric heating elements are expensive and inconvenient to use. The batteries for such devices are expensive and require long recharging times to be effective. Battery packs are bulky, add unnecessary weight for the user to carry and may interfere with the user's movements. A battery has the characteristic that as the ambient temperature decreases, the battery's power output decreases. Therefore, as the need for heat increases, the battery powered systems decrease in effectiveness.

German Pat. No. 3,544,856 to Walter discloses an insole that incorporates a heat dispensing material in a pocket formed in the insole padding. U.S. Pat. No. 4,658,515, issued Apr. 21, 1987 to Oatman discloses a laminated insole having pockets filled with an insulating material. The outer surfaces are formed of a heat reflective material. U.S. Pat. No. 4,249,391, issued Feb. 10, 1981 to Yoshida discloses footwear suitable for use as a house slipper having porous bags containing an exothermic agent. Yoshida discloses the use of small holes in the porous bags to facilitate heat flow from to a wearer's foot.

The prior art heated insole devices are unsuitable for long term wear in a shoe, boot or the like. The problem of cold feet for people engaging in outdoor activities in cold weather remains unsolved by the prior art.

SUMMARY OF THE INVENTION

The present invention provides an inexpensive solution to the problems of cold feet suffered by individuals who work or participate in outdoor recreational activities in cold weather. The present invention adds no extra weight and is easy and comfortable to use in a shoe or boot.

An insole for a boot or the like according to the present invention comprises an upper layer formed of a resilient material and a padding layer having an upper side connected to the upper layer. The padding layer is preferably formed in the general shape of the outline of human foot to have a toe portion and a heel portion. A section in the toe portion of the padding layer has a reduced thickness, and a pair of ledges are formed on opposite sides of the reduced thickness section. A cover plate is placed over the reduced thickness section. The front and rear edges of the cover plate extend over the ledges so that the cover plate and the reduced thickness portion of the padding layer define an open sided cavity formed to hold a heat source.

The cover plate is preferably formed of a rigid material having a plurality of holes therein to permit the passage of air through the cover plate to the heat source. The cover plate preferably is stitched to the ledges. The reduced thickness section is forward of the ball of the foot of a user's foot.

The padding layer preferably is formed of a material having flexibility sufficient to relieve shear stress at the connections between the cover plate and the padding layer when the insole flexes in the toe portion. The cover plate preferably is sufficiently rigid to stabilize the heat source and maintain it in a predetermined configuration to assure comfort to the foot of a user.

The reduced thickness portion of the padding layer preferably is at least about 12 mm from the toe end of the insole so that the toe end of the insole may be trimmed to adjust the length of the insole.

An insole for a boot or the like according to the present invention may also comprise an upper layer of a resilient material and a padding layer having an upper side connected to the upper layer. A stabilizer layer is connected to a lower side of the padding layer. The upper layer, the padding layer and the stabilizer layer are formed in the general shape of the outline of a human foot to have a toe portion and a heel portion. A cavity is formed in the padding layer so that a heat source may be placed therein. The heat source may be a commercially available device that produces heat from an exothermic chemical reaction.

The cavity is preferably located in the toe portion of the padding layer. The upper layer preferably has a plurality of holes therein for facilitating heat transfer from the heat source to the foot of a person using the insole.

A pull cord may be connected to the stabilizer layer for facilitating removal of the insole from a boot or the like.

DESCRIPTION OF THE PREFERRED EMBODIMENT

Figure 1:
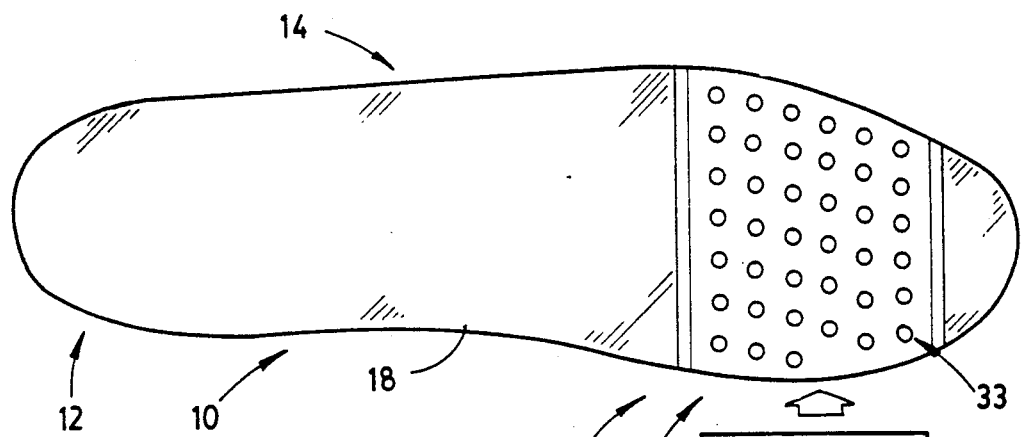
FIG. 1 is a top plan view of a foot warmer insole according to the present invention.
Figure 2:
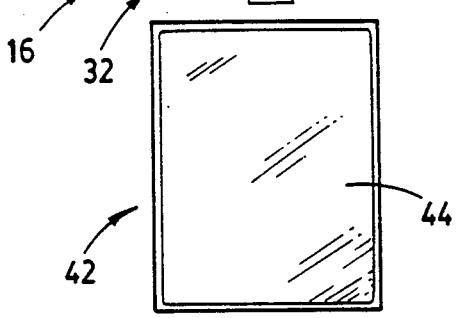
FIG. 2 is a side elevation view of the foot warmer insole of FIG. 1.

Referring to FIGS. 1 and 2, a foot warmer insole 10 according to the present invention includes a heel portion 12, an arch portion 14 and a toe portion 16. It should be noted that noe of the drawings are to any particular scale. The relative sizes of the features illustrated are for convenience and clarity of presentation only.

The foot warmer insole 10 includes an upper layer 18 that is preferably formed of a flexible material such as vinyl or the like. The upper layer 18 preferably has a thickness of about 0.05 to 0.10 inch. Any material suitable for making an upper surface of an insole for a boot or shoe may be used to form the upper layer 18. The upper layer 18 has an outline that generally conforms to the shape of a human foot.

Figure 3:
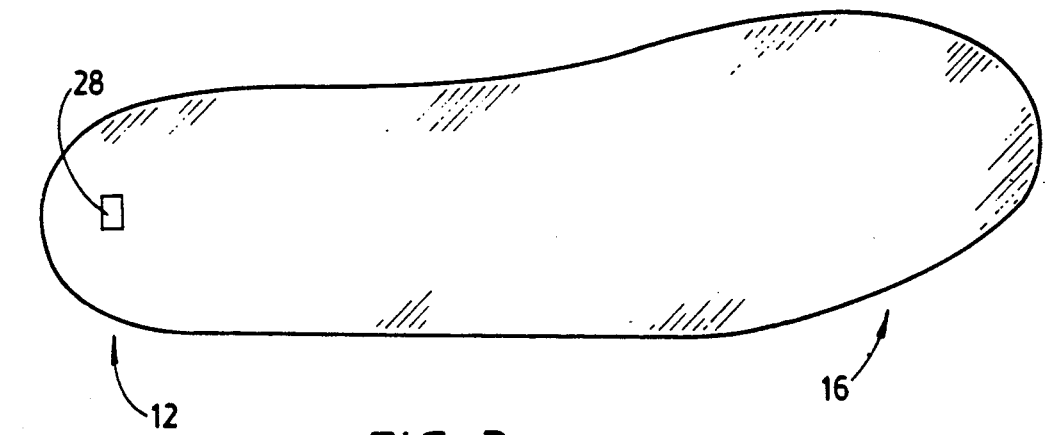
FIG. 3 is a bottom plan view of the foot warmer insole of FIGS. 1 and 2.

Referring to FIGS. 2 and 3, the foot warmer insole 10 includes a lower portion 20 that has an outline substantially identical to that of the upper surface 12. The lower portion 20 preferably includes at least a pair of stabilizer sheets 22 and 24.

A pull cord 26 may be connected to the inner stabilizer sheet 22 and arranged to pass through the outer stabilizer sheet 24 at a slot 28. The slot 28 may be in any convenient location near the heel portion 12 of the foot warmer insole 10, but is preferably about 0.5 to 0.75 inch from the heel end. The foot warmer insole 10 is designed to fit inside a boot or the like. The preferred location of the slot 28 permits the foot warmer insole 10 to be trimmed to fit various boot sizes. When the foot warmer insole 10 is inside a boot, the pull cord 26 folds over the upper layer 18 at the heel end so that the free end of the pull cord 26 is easily accessible so that it may be manually grasped to pull the foot warmer insole 10 out of the boot.

Referring to FIG. 3, most of the space between the upper layer 18 and the lower portion 20 is filled with a padding 30 formed of any suitable material, such as polyurethane foam.

Referring to FIGS. 1 and 2, a cavity 32 may be formed between the upper layer 18 and the lower portion 20. This cavity 32 preferably begins about 0.5 inch from the toe end of the foot warmer insole 10 and extends for a length of about 2.0 to 2.25 inches. In the toe region 16 of the foot warmer insole 10 the upper layer 18 and the lower portion 20 are separated by about 0.15 to 0.25 inches, which determines the thickness of the cavity 32. The upper layer 18 preferably includes a plurality of holes 33 in the portion that covers the cavity 32.

The dimensions of the cavity 32 are exemplary only. The invention is not limited in scope to any of the particular dimensions given herein. The essential characteristic of the cavity 32 is that it have dimensions suitable for receiving a heat source 42 therein. There are commercially available heat sources available that are suitable for placement in the cavity 32. One preferred heat source 42 comprises a mixture of iron powder, water, salt, activated charcoal and wood fiber in a pouch 44. The pouch 44 is preferably formed of a fabric that retains the material therein while permitting the entrance of air into the pouch 44. The heat source 42 is packaged in an air-tight container such as a cellophane envelope (not shown) for storage.

When the heat source 42 is removed from the envelope, air passes through the fabric. Exposure of the material inside the pouch 44 to oxygen causes an exothermic chemical reaction to begin. The pouch 44 should be exposed to the air for a brief time to allow the reaction to bring the pouch 44 to a temperature high enough to provide the desired amount of warmth. The rate and duration of the reaction depends upon the amount of air to which the pouch is exposed. Outside the boot, when the pouch is exposed to oxygen, it heats rapidly to about 120° F. Inside a boot where there is only a small amount of oxygen, the heater will maintain a temperature near body temperature for about six hours. Removing the boot from the wearer's foot for a few minutes allows more oxygen to reach the heat generating materials in the pouch 44 and cause the heater to again reach a temperature of about 120° F. The preferred heating element is odorless and produces no harmful fumes.

To use the foot warmer insole 10, the existing insoles should be removed from the boots or shoes. The foot warmer insole 10 should be slightly shorter than the existing insoles to provide ease of removal and insertion. Socks should be worn while using the foot warmer insole 10 to prevent the possibility of excessively warming portions of the user's feet. For best results one thin pain of ski socks or the like should be worn while using the foot warmer insole 10.

After the heating element has been exhausted, it is slid laterally out of the cavity. If additional heat is desired, then a new heater is inserted in the cavity.

Figure 4:
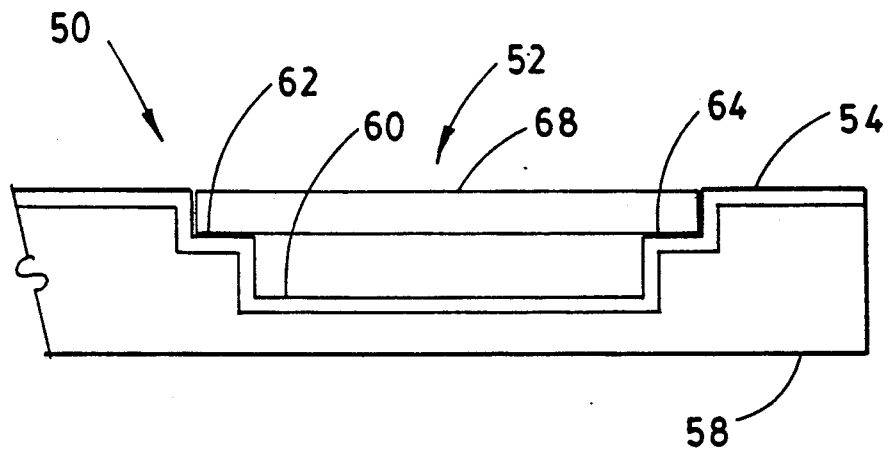
FIG. 4 is an elevation view of a second embodiment of an insole according to the present invention showing structure for forming a cavity for containing a heating element.
Figure 5:
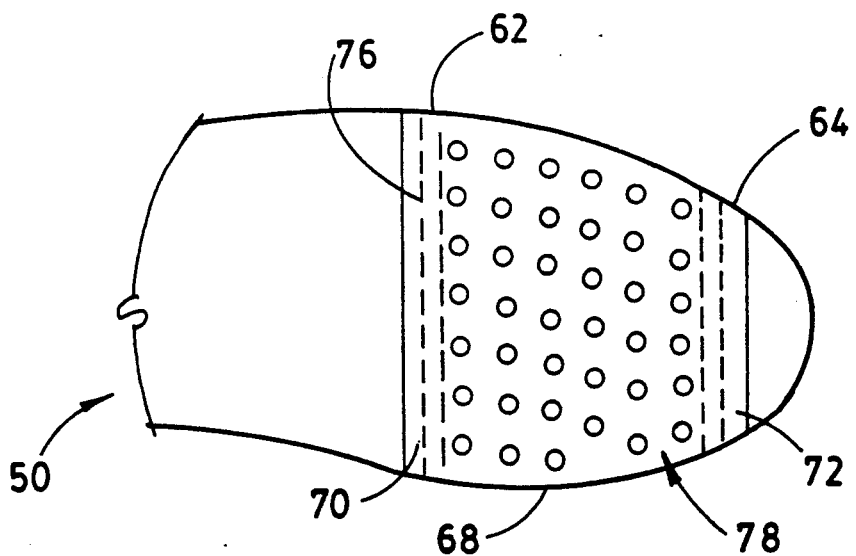
FIG. 5 is a partial plan view of the insole of FIG. 4.

FIG. 4 shows the front portion of a preferred structure for an insole 50 that includes a recess 52 for receiving the heating pouch 44. The insole 50 is preferably an orthotic insole that has sufficient rigidity to permit to be inserted into a shoe or boot without bending appreciably. The insole 50 is first formed to have an upper layer 54 that may be formed of a vinyl or fabric material. A cushioning layer 58 that preferably comprises a material formed of polyurethane foam or the like is attached to the upper layer 52. The cushioning layer 58 is bonded to the upper layer 54 in a conventional manner. The overall thickness of the front portion of the insole 50 is preferably about 5.0 mm.

The recess 52 comprises a central portion 60 and ledges 62 and 64 at the front and rear ends of the central portion 60. The length of the central portion is preferably about 57 mm. The ledges 62 and 64 extend across the width of the insole 50 and are about 6.25 mm long. The ledge 64 preferably begins about 12 or 13 mm from the front edge 65 of the insole. The distance of the ledge from the end 65 of the insole 50 should be sufficiently large to permit trimming so that the insole 50 may be customized to allow for minor variations in the length of the inside of the boot or shoe with which it is to be used.

The ball of the foot bears a large part of the user's weight. The heating element generally does not provide the desired amount of cushioning. The length of the recess 52 must therefore be sufficient to hold the heating element 42 so that it will be flat and forward of the ball of the wearer's foot to avoid interfering with the cushioning at the ball of the foot.

The central portion 60 and the ledges 62 and 64 may be formed by compressing the insole. The insole 50 is crushed so that the central portion 60 has a thickness of about 0.5 mm. The thickness of the insole 50 at the ledges 62 and 64 is preferably about 4.5 mm. The process of crushing the insole 50 to form the recess 52 may include applying both heat and pressure to permanently deform the insole where the recess 52 is formed.

A cover plate 68 is placed over the recess 52 and preferably secured by sewing with stitches 76 the edges 72 and 74 to the ledges 62 and 64, respectively. The cover plate 68 may also be secured to the ledges 62 and 64 by an adhesive or by using both an adhesive and stiching. The cover plate 68 preferably has a length of about 69 mm and a thickness of about 0.5 mm. These dimensions of the cover plate allow it to fit on the ledges 62 and 64 without extending above the 5 mm thickness of the insole 50 in front of and behind the ledges 62 and 64. The central portion 60 of the recess 52 accommodates a heating pouch 44 that has thickness of about 3.5 mm.

The cover plate 68 is preferably formed of a material such as polycarbonate. The upper surface 69 of the cover plate 68 is preferably brushed so that it has a velvet finish. The brushed upper surface 69 of the cover plate 58 prevents excessive sliding of the user's foot on the toe portion of the insole 50.

The cover plate preferably includes a plurality of holes 78 that are about 4.75 mm in diameter. The holes allow adequate oxygen to enter the heat pack.

The cover plate is preferably formed of a rigid material such as polycarbonate or the like to stabilize the heat pack and keep it flat while it is inside the recess. If the cover plate is not sufficiently rigid, then the heat pack tends to bunch up under the user's foot and causes discomfort. The cushioning layer 58 is preferably flexible. When the user walks, the insole 52 tends to bend in the toe portion. The flexibility of the cushioning layer 58 allows the insole 52 to bend without causing undesirable large shear stresses at the connections between the cover plate and the ledges 62 and 64.

The cushioning material must be sufficiently dense that the weight of the user does not compress the insole below the heating pack and its cover. Otherwise there might be a bulge that would cause discomfort in the user's the toe region The structures and methods disclosed herein illustrate the principles of the present invention. The invention may be embodied in other specific forms without departing from its spirit or essential characteristics. Therefore, the described embodiments are to be considered in all respects as exemplary and illustrative rather than restrictive. Therefore, the appended claims rather than the foregoing description define the scope of the invention. All modifications to the embodiments described herein that come within the meaning and range of equivalence of the claims are embraced within the scope of the invention.

What is claimed is:

1. An insole for a boot or shoe, comprising:
   a heat source;
   an upper layer of a resilient material;
   a padding layer connected to the upper layer, the upper layer and the padding layer being formed to have a periphery that is in the general shape of the outline of the sole of a human foot and having a heel portion and a toe portion so that the insole will fit inside a boot or shoe;
   a compressed section in the toe portion extending across the toe section, the compressed section having a pair of ledges on opposite sides thereof that define front and rear edges of the compressed section; and
   a cover plate placed over the compressed section and having edges connected by stitching to the front and rear edges of the compressed section to define a cavity for holding the heat source therein, the cover plate being sufficiently rigid to stabilize the shape of the heat source and maintain it in a flattened configuration to assure comfort to the foot of a person wearing a boot or shoe in which the insole is inserted, the cover plate having a thickness such that the cover plate does not extend beyond the thickness of the insole adjacent the front and rear edges of the compressed section.

2. The insole of claim 1 wherein the front edge of the compressed section in the padding layer is about 0.5 inch from the toe end of the insole so that the toe end of the insole may be trimmed to adjust the length of the insole.

3. The insole of claim 2 wherein the cover plate is formed of polycarbonate having a brushed upper surface to prevent excessive sliding of the foot of a person wearing a boot or shoe in which the insole is inserted.

4. The insole of claim 3, wherein the cavity is formed in a toe portion of the insole structure.

5. The insole of claim 1, wherein the cover plate is connected by stitching to the front and rear ledges so as to maintain a substantially consistent top surface across the compressed section of the insole structure.

6. The insole of claim 1, wherein the cover plate has a plurality of holes formed therewithin.

7. The insole of claim 1, wherein the cover plate is formed of polycarbonate.

8. The insole of claim 1, wherein the cover plate has a brushed upper surface to prevent sliding of the foot.

9. The insole of claim 1, wherein the heat source is replaceably fitted within the compressed section.

* * * * *